United States Patent [19]

Mittleman

[11] 4,000,740
[45] Jan. 4, 1977

[54] INJECTION SITE

[75] Inventor: Herbert Mittleman, Deerfield, Ill.

[73] Assignee: Baxter Travenol Laboratories, Inc., Deerfield, Ill.

[22] Filed: Aug. 15, 1975

[21] Appl. No.: 605,170

Related U.S. Application Data

[63] Continuation of Ser. No. 475,215, May 31, 1974, abandoned.

[52] U.S. Cl. .................... 128/214 R; 210/DIG. 23
[51] Int. Cl.² ........................................ A61M 5/14
[58] Field of Search ........ 128/214 R, 214 C, 214.2, 128/227; 55/159, 190, 199; 210/DIG. 23, 436

[56] References Cited

UNITED STATES PATENTS

| 2,999,499 | 9/1961 | Willet | 128/214 R |
| 3,025,855 | 3/1962 | Hamilton | 128/214 C |
| 3,216,418 | 11/1965 | Scislowicz | 128/214 C |
| 3,332,418 | 7/1967 | Brody | 128/214 R |
| 3,778,973 | 12/1973 | Martinez | 55/199 |
| 3,886,937 | 6/1975 | Bobo et al. | 128/214 R |
| 3,905,905 | 9/1975 | O'Leary et al. | 210/436 |

Primary Examiner—Dalton L. Truluck
Attorney, Agent, or Firm—Paul C. Flattery; George H. Gerstman

[57] ABSTRACT

An injection site is provided in the illustrative embodiment, in which a first inlet (to which a parenteral fluid conduit is connected) and a second inlet (adapted to receive injected medication) are parallely located on one end of a main body portion. An outlet is located on the opposite end of the main body portion, with the second inlet and the outlet being substantially coaxial. The main body portion defines a single chamber that communicates with the inlets and outlet and is constructed to provide unobstructed flow of the parenteral liquid and medication to the outlet.

18 Claims, 12 Drawing Figures

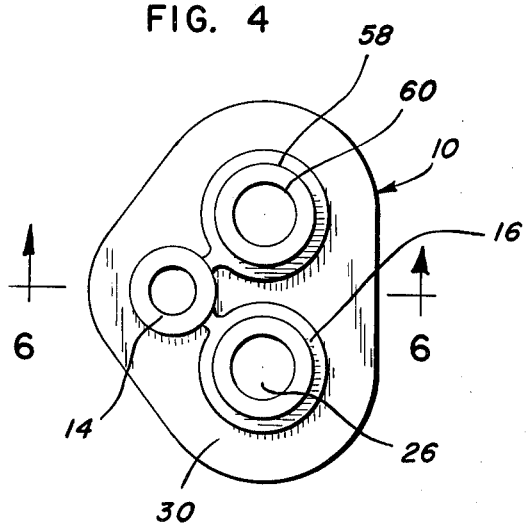
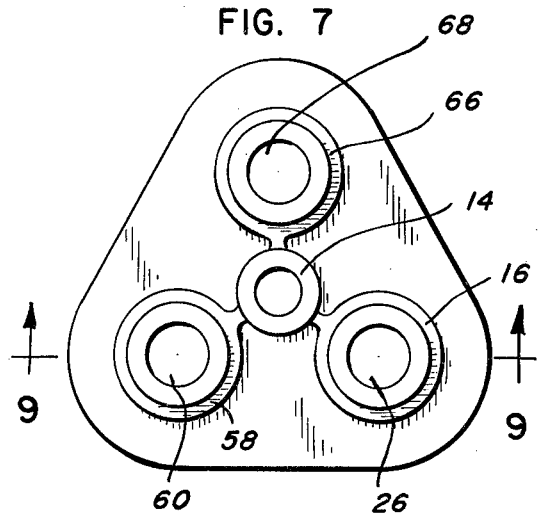
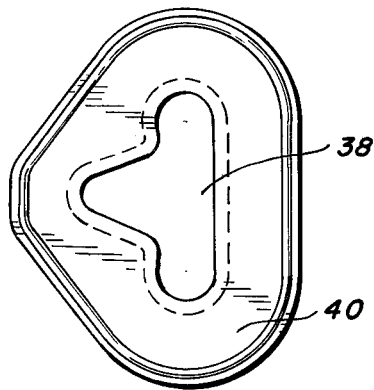
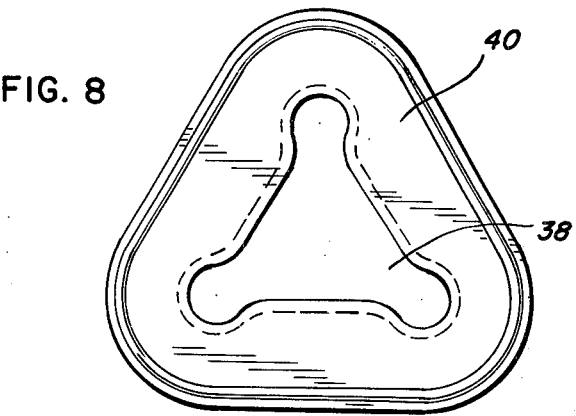
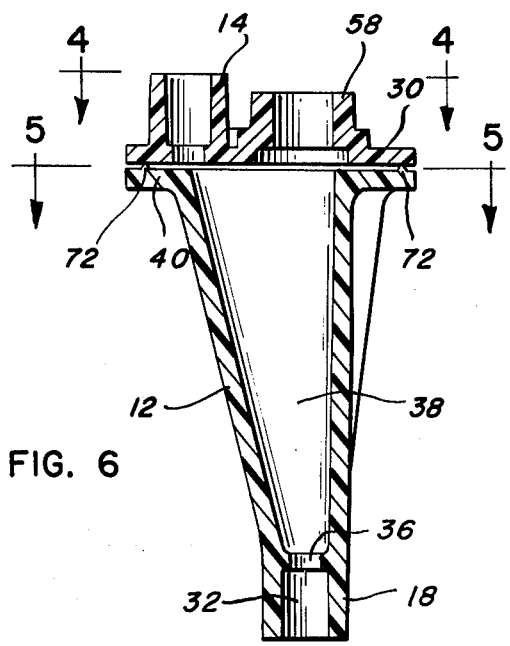
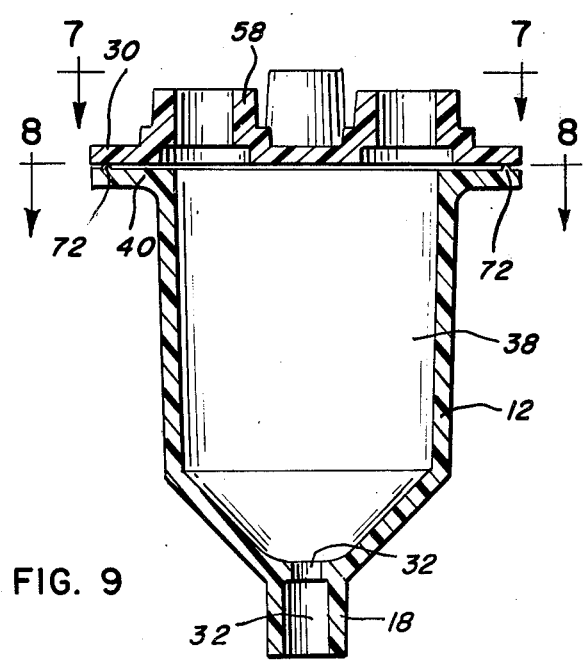

INJECTION SITE

This is a continuation of application Ser. No. 475,215, filed May 31, 1974, and now abandoned.

BACKGROUND OF THE INVENTION

This invention relates to an improved injection site.

Injection sites are commonly used in hospitals where a parenteral fluid is being fed to a patient intravenously and it is also desired to combine another medicament with the parenteral fluid. In such circumstances, the parenteral fluid is fed via flexible conduit to one inlet of a connecting device, commonly called an injection site. Flexible conduit extends from the outlet of the injection site to an appropriate device for administering the liquid to the patient. The injection site typically carries a second inlet, having a pierceable diaphragm connected thereto. The supplementary medicament is injected into the second inlet by a hypodermic syringe and it becomes combined with the parenteral liquid for administration to the patient.

One widely used type of injection site is commonly known as a Y-site. In a conventional Y-site, a generally Y-shaped tube couples the flexible parenteral fluid conduit to a flexible outlet conduit, with the straight leg of the "Y" being connected to the ends of the coupled flexible conduit and with the angular arm of the Y feeding into the center of the coupling leg.

One of the deficiencies of the aforementioned Y-site is that the area of the outlet is no larger than the area of either inlet, and due to this construction, turbulence can be caused at the junction of the straight leg and the angled arm of the Y. In addition, the travel of the hypodermic syringe's needle is limited by the length of the angular arm, and thus the needle may easily strike the wall of the straight leg of the Y. A further defect of this prior art Y-site is that the bends therein increase the possibility of material being incrusted in the tube.

Another prior art injection site is disclosed in the U.S. patent to Brody, U.S. Pat. No. 3,332,418. In Brody's injection site, there is possible turbulence at the junction of the inlets, due to the inwardly extending shoulders which impede the smooth flow of fluid. In addition, the construction of Brody's injection site permits the operator to easily strike an interior wall with the needle of the hypodermic syringe. Further, the inwardly extending shoulders of the Brody injection site increase the possibility of material becoming incrusted in the device.

In addition to the above deficiencies, the structures of the first mentioned Y-site and the Brody injection site require relatively complex molding. For example, the first mentioned Y-site requires three cores due to its angular configuration.

Accordingly, it is an object of the present invention to provide an injection site that alleviates turbulent flow at the junction of the inlets and instead provides relatively smooth flow.

Another object of the present invention is to provide an injection site which alleviates the problem of striking an inside wall of the injection site with the hypodermic needle.

A further object of the present invention is to provide an injection site which provides a substantially continuous or straight through flow path for the material going through the injection site.

A still further object of the present invention is to provide an injection site which aids in preventing material from becoming incrusted inside the device.

Another object of the present invention is to provide an injection site that is simple to manufacture and is relatively inexpensive to produce.

A further object of the present invention is to provide an injection site which is easy for the operator to use.

A still further object of the present invention is to provide a multi-inlet injection site, which is simple to manufacture and provides good laminar flow.

Other objects and advantages of the present invention will become apparent as the description proceeds.

BRIEF DESCRIPTION OF THE INVENTION

In accordance with the present invention, there is provided an injection site having a first inlet to which a conduit from a first liquid container is adapted to be connected, a second inlet adapted to receive injected medication, and an outlet through which the combined first liquid and injected medication can flow with the outlet adapted for coupling to another conduit. A main body portion couples the first and second inlets to the outlet. The main body portion defines a chamber that communicates with the first and second inlets and the outlets.

In an illustrative embodiments, the chamber has a cross-sectional area at least at some portion thereof that is substantially greater than the cross-sectional area of the first inlet. The chamber is constructed to provide unobstructed flow of the first liquid and medication to the outlet.

In the illustrative embodiments, a pierceable, resealable diaphragm is connected to the second inlet with a compression fit. The first and second inlets are parallely positioned and the second inlet and the outlets are substantially coaxial, so that a long hypodermic needle can be pushed straight through.

A more detailed explanation of the invention is provided in the following description and claims, and is illustrated in the accompanying drawings.

BRIEF DESCRIPTION OF THE DRAWINGS

FIG. 4 is a top plan view of an injection site according to another form of the invention, and taken along the plane of the line 4—4 of FIG. 6;

FIG. 5 is a cross-sectional view of an injection site taken along the plane of the line 5—5 of FIG. 6;

FIG. 6 is a cross-sectional view of an injection site, taken along the plane of the line 6—6 of FIG. 4;

FIG. 7 is a top plan view of another firm of an injection site constructed in accordance with the principles of the invention, and taken along the plane of the line 7—7 of FIG. 9;

FIG. 8 is a cross-sectional view of an injection site, taken along the plane of the line 8—8 of FIG. 9;

FIG. 9 is a cross-sectional view of an injection site, taken along the plane of the line 9—9 of FIG. 7;

DETAILED DESCRIPTION OF THE ILLUSTRATIVE EMBODIMENT

Figures 1, 2, 3:
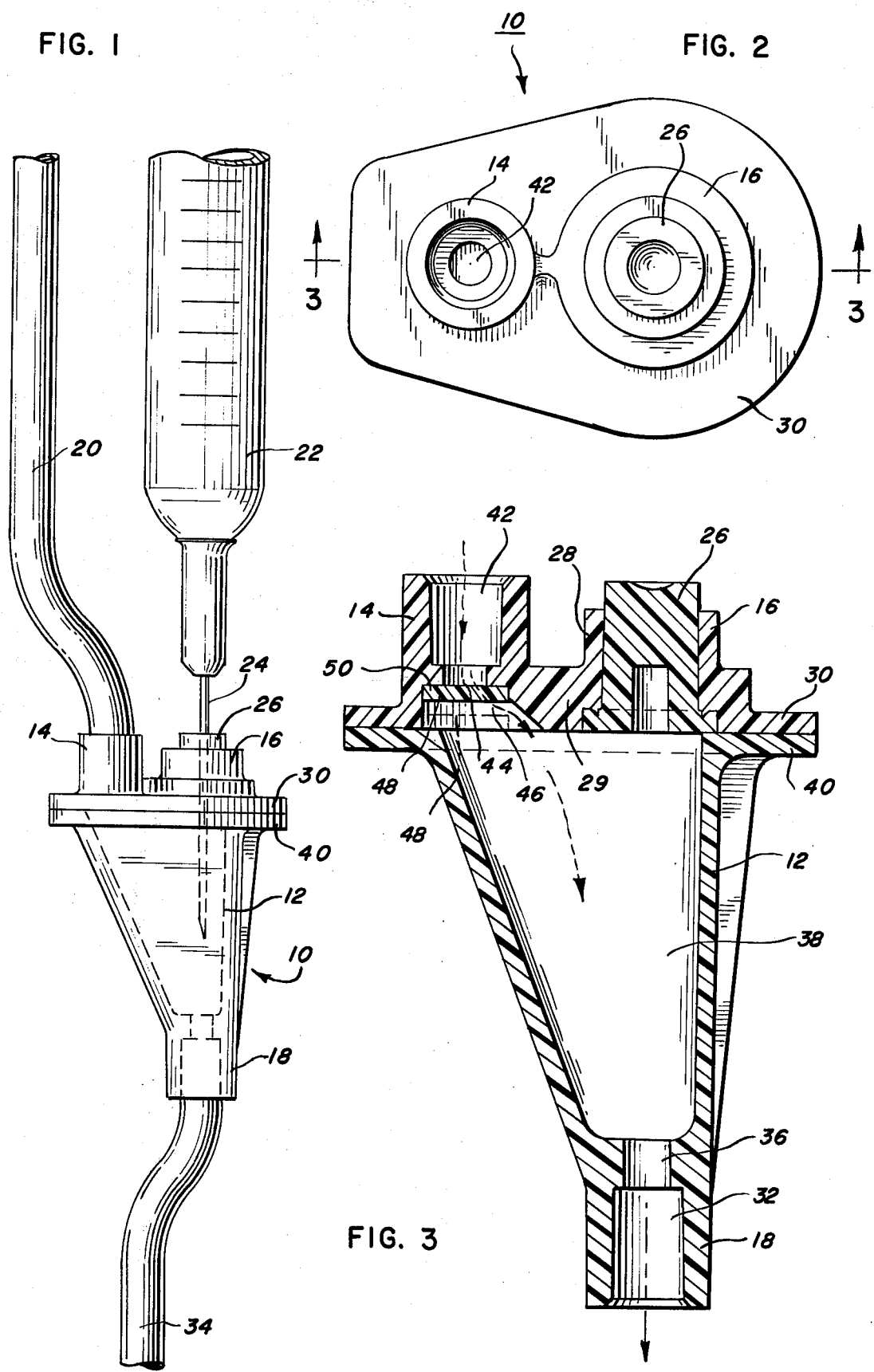
FIG. 1 is a front view of an injection site constructed in accordance with the principles of the present invention, being used with parenteral liquid conduit and a hypodermic syringe.
FIG. 2 is a top plan view of an injection site constructed in accordance with the principles of the present invention.
FIG. 3 is a cross-sectional view thereof, taken along the plane of the line 3—3 of FIG. 2.

Referring to FIG. 1, there is shown an injection site 10 having a main body portion 12, a first inlet 14, a second inlet 16 and an outlet 18. Flexible plastic conduit 20 has its downstream end coupled to first inlet 14 and its upstream end is connected to a parenteral liquid container (not shown).

A conventional hypodermic syringe 22 is shown with its needle 24 extending into second inlet 16, through a pierceable, resealable diaphragm 26. A diaphragm formed of latex has been found satisfactory. As shown most clearly in FIG. 3, diaphragm 26 is held under compression by the circular upright wall 28 defining inlet 16. This obviates the need to use to a plastic shrink band, as with prior art constructions. Further, this increases the resealing qualities of the diaphragm.

Inlets 14 and 16 are formed of a non-pierceable plastic material and are molded in a unitary assembly 29 including first inlet 14, second inlet 16 and a circumferential flange 30. Assembly 29 has a generally planar bottom surface, except for the flow path openings of the inlets.

Body portion 12 is also formed of a non-pierceable plastic material and includes outlet 18, a relatively large orifice 32 to which flexible outlet conduit 34 is connected, and a smaller opening 36 coupling orifice 32 with a chamber 38.

The walls defining chamber 38 are continuous and smooth, and by utilizing such a construction, the fluids flowing into the inlets will have laminar flow through channel 38 without any obstruction shoulders or the like.

The cross-sectional area of the top of chamber 12 is substantially greater than the cross-sectional area of the sum of the flow passage of the first inlet 14, the second inlet 16 and the outlet 18. As a specific example, although no limitation is intended, the bore of inlet 14 has a 0.1 inch diameter, the bore of inlet 16 (which corresponds to the diameter of diaphragm 26) has a diameter of 0.2 inch and the diameter of outlet opening 36 is 0.1 inch, with the total area of all three openings equalling 0.0471 inch. The top of chamber 38 has an area of 0.0783 inch which is 66 percent greater than the total area of all the inlet and outlet ports.

Throughout its entire length, the cross-sectional area at any point along chamber 38 is greater than the cross-sectional area of the flow path of first inlet 14. Taking this into account, with the continuous smooth wall surface of chamber 38, good laminar flow is provided through chamber 38.

Main body member 12 has a circumferential flange 40 at its top, which is fastened to circumferential flange 30 of top member 28 by sonic welding the two together. It can be seen that only two separate molded parts are required and these parts are fastened together to form the basic injection site.

Circumferential flanges 30 and 40 together form a fender which is useful to raise the injection site above the contaminated area when the site is taped to the body. The fender extends in a direction perpendicular to the axes of the inlets. In the event the needle slips the flange may act as a shield. In addition, the fender acts to alleviate the problem of hooking on to protrusions.

As shown in FIG. 3, the flow path of inlet 14 comprises a main opening 42 to which conduit 20 is connected, an orifice 44 and a large opening 46 communicating with chamber 38. In assembling the injection site of FIG. 3, a check valve 48 comprising a plastic disc is press-fitted to seat against an annular inverted shoulder 50. In this manner, upward fluid flow is prevented but downward fluid flow via openings 42 and 44 will force disc 48 downwardly to release it from shoulder 50 and thereby open the fluid path as can readily be seen in FIG. 3.

Mofified forms of the invention are shown in FIGS. 4–6, FIGS. 7–9 and FIGS. 10–12. In the embodiments of FIGS. 4–12, the same reference numerals as those used in the FIGS. 1–3 embodiment are used to show similar structure.

Figure 10:
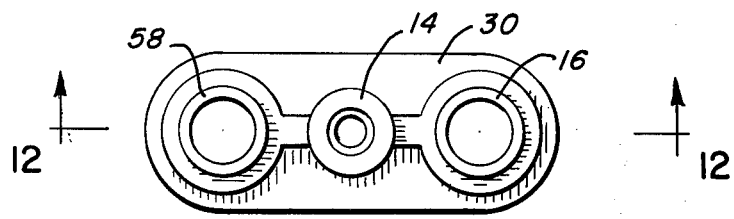
FIG. 10 is a top plan view of another form of an injection site constructed in accordance with the principles of the invention, and taken along the plane of the line 10—10 of FIG. 12.
Figure 11:
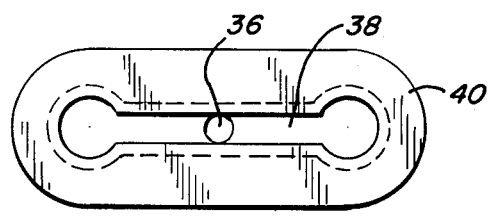
FIG. 11 is a cross-sectional view of an injection site, taken along the plane of the line 11—11 of FIG. 12.
Figure 12:
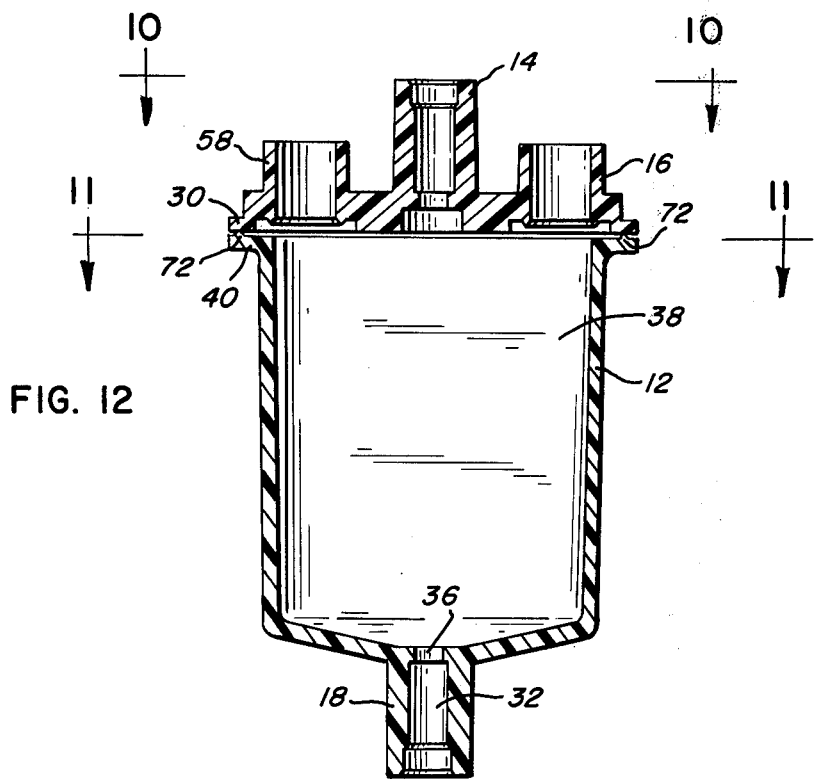
FIG. 12 is a cross-sectional view of an injection site, taken along the plane of the line 12—12 of FIG. 10.

In the FIGS. 4–6 embodiment, a third inlet 58 is provided having a pierceable, resealable diaphragm 60 compression fitted therein. In the FIGS. 7–9 embodiment, a fourth inlet 66 is provided having a pierceable, resealable diaphragm 68 compression fitted therein. First inlet 14 is centrally located with inlets 16, 58 and 66 forming a substantially equilateral triangle and with main body 12 being generally symmetrical about the axis of inlet 14. In the FIGS. 10–12 embodiment, three inlets 14, 16 and 58 are provided as in the FIGS. 4–6 embodiment, but the inlets are collinear in plan view, as seen in FIG. 10.

The embodiments of FIGS. 4–6, FIGS. 7–9 and FIGS. 10–12 have the advantages of the FIGS. 1–3 embodiment, in that the construction is such as to provide good laminar flow, simplicity in construction and ease of use. In all of the embodiments, the cross-sectional area of the chamber at its top is substantially greater than the sum of the cross-sectional areas of all of the inlets and outlet.

In addition, in all embodiments the outlet is substantially coaxial with the injection inlet, so that the hypodermic needle can extend through the device without striking an inner wall.

The single chamber design of the embodiment of the present invention enhances one's ability to clear air from the prior art Y-site as it must be inverted and tapped repeatedly to coax air out of the side arm of the Y.

In FIGS. 6 and 9, the top assemblies 29 are shown slightly separated from the body portions 12. This illustrates the construction prior to sonic welding, wherein an annular upstanding protuberance 72 is utilized as is known in the art of sonic welding. It is to be understood, however, that other, equivalent fastening means may be utilized according to the invention.

Additionally, while one injection port is shown in each embodiment having a pierceable diaphragm, one or more of the other inlet ports may be used as injection ports and thus additional diaphragms would be used. While a compressionfit diaphragm is shown as preferred, in some instances it may be desired to use a diaphragm that extends over the upright inlet wall. Thus it is to be understood that various modifications and substitutions may be made by those skilled in the art without departing from the novel spirit and scope of the invention.

What is claimed is:

1. An injection site for location between a parenteral source of fluid and a patient, which comprises: a first inlet to which a conduit from a first liquid container is adapted to be connected; a second inlet adapted to receive needle-injected medication; an outlet through which the combined first liquid and injected medication can flow with said outlet adapted for coupling to a conduit; a main body portion defining a single chamber that communicates with said first and second inlets and said outlet, said chamber having a sloped wall between said first inlet and said outlet, said chamber having a cross-sectional area adjacent said first and second inlets that is greater than the cross-sectional area of said chamber adjacent said outlet, said chamber having a cross-sectional area that is substantially greater than the cross-sectional area of said first inlet; said second inlet and said outlet being substantially coaxial, whereby the needle is substantially prevented from piercing the chamber, and said chamber being constructed to provide unobstructed flow of the first liquid and medication to said outlet; and a check valve located in said first inlet and adjacent said chamber.

2. In an injection site as described in claim 1, including a pierceable, resealable diaphragm connected to said second inlet with a compression fit.

3. In an injection site as described in claim 1, said main body portion and outlet being formed of a non-pierceable plastic material.

4. An injection site as described in claim 1, said first and second inlets being parallelly positioned.

5. In an injection site as described in claim 1, including a third inlet in communication with said chamber; said first, second and third inlets being parallely positioned.

6. In an injection site as described in claim 5, including a pierceable, resealable diaphragm connected to said second inlet with a compression fit.

7. In an injection site as described in claim 5, and further including a fourth inlet in communication with said chamber; said first, second, third and forth inlets being parallely positioned.

8. An injection site as described in claim 7, including a pierceable, resealable diaphragm connected to said second inlet with a compression fit.

9. An injection site as described in claim 1, including fender means extending from said site in a direction transverse the axis of said second inlet.

10. An injection site as described in claim 9, said fender means comprising a circumferential flange.

11. An injection site for location between a parenteral source of fluid and a patient, which comprises: a first inlet to which a conduit from a first liquid container is adapted to be connected; a second inlet adapted to receive needle-injected medication; an outlet through which the combined first liquid and injected medication can flow with said outlet adapted for coupling to a conduit; a main body portion coupling said first and second inlets to said outlet, said second inlet and said outlet being substantially coaxial, whereby the needle is substantially prevented from piercing the chamber; said main body portion defining a single chamber the wall of which is continuous and without projections, said chamber communicating with said first and second inlets and said outlet; said chamber having a sloped wall between said first inlet and said outlet with said chamber having a cross-sectional area adjacent said first and second inlets that is greater than the cross-sectional area of said chamber adjacent said outlet; and a check valve located in said first inlet and adjacent said chamber.

12. An injection site as described in claim 11, wherein said chamber has a cross-sectional area that is substantially greater than the cross-sectional area of said first inlet; and a pierceable, resealable diaphragm connected to said second inlet with a compression fit.

13. An injection site as described in claim 11, including a third inlet in communication with said chamber, said first, second and third inlets all being parallely positioned.

14. An injection site as described in claim 11, wherein said main body portion and oulet are formed of a non-pierceable plastic material and said outlet and said second inlet are substantially coaxial; and a pierceable, resealable diaphragm connected to said second inlet with a compression fit.

15. An injection site as described in claim 11, including fender means extending from said site in a direction transverse the axis of said second inlet.

16. An injection site as described in claim 15, said fender means comprising a circumferential flange.

17. An injection site comprising a first inlet to which a conduit from a first liquid container is adapted to be connected; a second inlet adapted to receive injected medication; an outlet through which the combined first liquid and injected medication can flow with said outlet adapted for coupling to a conduit; a main body portion defining a single chamber that communicates with said first and second inlets and said outlet, said chamber having a cross-sectional area that is substantially greater than the cross-sectional area of said first inlet; and said chamber being constructed to provide unobstructed flow of the first liquid and medication to said outlet; and further including a check valve located in said first inlet and adjacent said chamber, said check valve comprising a disc normally in an uppermost position of a valve chamber to block fluid flow, but adapted to be forced downwardly in said valve chamber during use of said injection site to permit fluid flow.

18. An injection site comprising a first inlet to which a conduit from a first liquid container is adapted to be connected; a second inlet adapted to receive injected medication; an outlet through which the combined first liquid and injected medication can flow with said outlet adapted for coupling to a conduit; a main body portion coupling said first and second inlets to said outlet, said main body portion defining a single chamber the wall of which is continuous and without projections, said chamber communicating with said first and second inlets and said outlet; said first and second inlets being parallelly positioned; and further including a check valve located in said first inlet and adjacent said chamber said check valve comprising a disc normally in an uppermost position of a valve chamber to block fluid flow, but adapted to be forced downwardly in said valve chamber during use of said injection site to permit fluid flow.

* * * * *